United States Patent [19]

Moore

[11] Plant 4,624

[45] Jan. 20, 1981

[54] ROSE PLANT

[76] Inventor: Ralph S. Moore, 2519 E. Noble Ave., Visalia, Calif. 93277

[21] Appl. No.: 71,922

[22] Filed: Sep. 4, 1979

[51] Int. Cl.[3] ..... A01H 5/00
[52] U.S. Cl. ..... Plt./10
[58] Field of Search ..... Plt./10

*Primary Examiner*—Robert E. Bagwill
*Assistant Examiner*—James R. Feyrer

[57] ABSTRACT

This invention relates to a new and distinct variety of miniature rose plant primarily distinguished by very double bright red flowers of carnation-like form borne in clusters and by the exceptionally long lasting quality of said flowers.

1 Drawing Figure

1

The present invention relates to a new and distinct variety of hardy, dwarf, bush, type rose plant of the miniature class; the variety being primarily characterized — as to novelty — by brilliant red flowers of a form and doubleness resembling that of a carnation and which in general color effect are similar to Fire Princess (miniature — U.S. Plant Pat. No. 3,084).

The variety is further characterized by:

An abundance of bloom, with flowers borne usually several to the stem in fairly tight clusters.

Little or no fragrance.

A plant which is vigorous, of rounded, upright shape with small semi-glossy foliage with pointed leaflets; the buds and flowers being similar in form and size to Fire Princess, but more double and slightly smaller.

The plant, which has a normal height of 12–14 inches or more, can easily be maintained at lesser height by occasional trimming.

A plant which grows and blooms satisfactorily both in greenhouse and outdoors; is especially good for growing in pots; and provides excellent garden decoration as well as cut flowers.

The present variety of miniature rose was originated by me at Sequoia Nursery located at Visalia, Calif., under conditions of careful control and observation, as a cross between Little Chief (miniature — not patented) as the seed parent and Fire Princess (miniature — U.S. Plant Pat. No. 3,084), as the pollen parent.

Subsequent to origination of the variety I successfully asexually reproduced it at Sequoia Nursery, located as aforesaid, by budding, as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Thunder Cloud.

Flowers borne: Singly but usually several together in clusters of 3 to 7 or more on slender wirey stems.

2

Quantity of bloom: Abundant both outside and in greenhouse.

Bud:

*Peduncle.*—Medium length; slender but sturdy; erect; medium green: with several very short hairs. Before calyx breaks; size — small. Form medium long to short; pointed with several to numerous foliaceous appendages and few hairs on surface of bud; with foliaceous parts extending beyond the tip of the bud equal to one-half or less of its length.

*Color.*—Medium green, occasionally tinted with bronze (outdoors). As calyx breaks, color — medium to dark red. Opening: opens well in all weather.

Bloom:

*Size when fully open.*—Small, averaging about 30–35 mm.

*Petalage.*—Very double — averaging about 75–80 petals, arranged regularly plus several small petaloids.

*Form.*—Full rounded, resembling a small full double carnation. Open flowers do not show stamens.

Petals: Fairly thick; satiny on inside and on outside surface.

*Shape.*—Outside petals, broad lanceolate (wedge shape) with rounded tip; intermediate — broad lanceoldate with acute (slightly pointed) tip; inside — lanceloate with pointed tip.

Color: Newly opened flower from a plant grown in plastic greenhouse (August 1979), Visalia, Calif.

*Outside petal.*—Outside surface — near Currant Red 821/1 with lighter (near white) area at base. Inside surface — near Orient Red 819/1 overlaid or veined with darker red, with small bluish or near white area at base.

*Intermediate petal.*—Outside surface near Currant Red 821/1 with lighter (near white) area at base. Inside surface similar to outside petal.

*Inner petal.*—Outside surface — same as intermediate petal; inside surface — same as intermediate petal. General color effect; newly opened flowers — bright red in direct sunlight almost a fluorescent orange red. Three days open — color gradually becomes less brilliant. Behavior — usually opens well in all weather. Spent petals hang on for a time then drop off. Flower longevity (July–August 1979) — plant in pot 6–10 days or longer. Cut flowers at living room temperature 5–7 days.

Reproductive organs:

*Stamens.*—Few — usually none.
*Filaments.*—Few — usually none.
*Anthers.*—Few — usually none.
*Pollen.*—None.
*Pistils.*—Average number.
*Styles.*—Slender — varying length.
*Stigmas.*—Absent or malformed.
*Ovaries.*—All enclosed in calyx.
*Hips.*—None.
*Sepals.*—Permanent; spear shaped; recurved.
*Seed.*—None.

Foliage:

*Leaves.*—Compound of five (sometimes three or seven) leaflets; medium small; leathery; semi-glossy.
*Leaflets.*—Shape; broad, nearly oval; apex acute; base rounded — sometimes acute. Margin serrate. Color: medium green; new growth — normal (medium) green (sometimes tinted reddish). Rachis: medium strength; upper side may have few or no thorns or tiny prickles, grooved; underside may have several thorns and few or no prickles. Stipules: medium long; medium width; medium to short length narrow points which turn out usually at about 45 degrees or more.

Growth:

*Habit.*—Dwarf; bushy; rounded; much branched.
*Growth.*—Free vigorous; internodes short.
*Canes.*—Medium; slender; sturdy.
*Main stems.*—Color: medium green.
*Thorns.*—Average; slender; inclined downward; color; brown. Prickles — none. Hairs — none.
*Branches.*—Color: medium green. Thorns: average; slender; inclined downward. Medium to short oval base. Prickles — none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit substantially as illustrated and described, characterized by very double flowers of a doubleness and form resembling that of a carnation, the buds and flowers resembling Fire Princess (miniature — U.S. Plant Pat. No. 3,084) in size and color; and further characterized by a plant which is vigorous, yet more compact than Fire Princess, said plant being easy to propagate from cuttings, or by budding, with an abundance of small to medium size semi-glossy foliage and an abundance of flowers borne usually in small to medium size clusters.

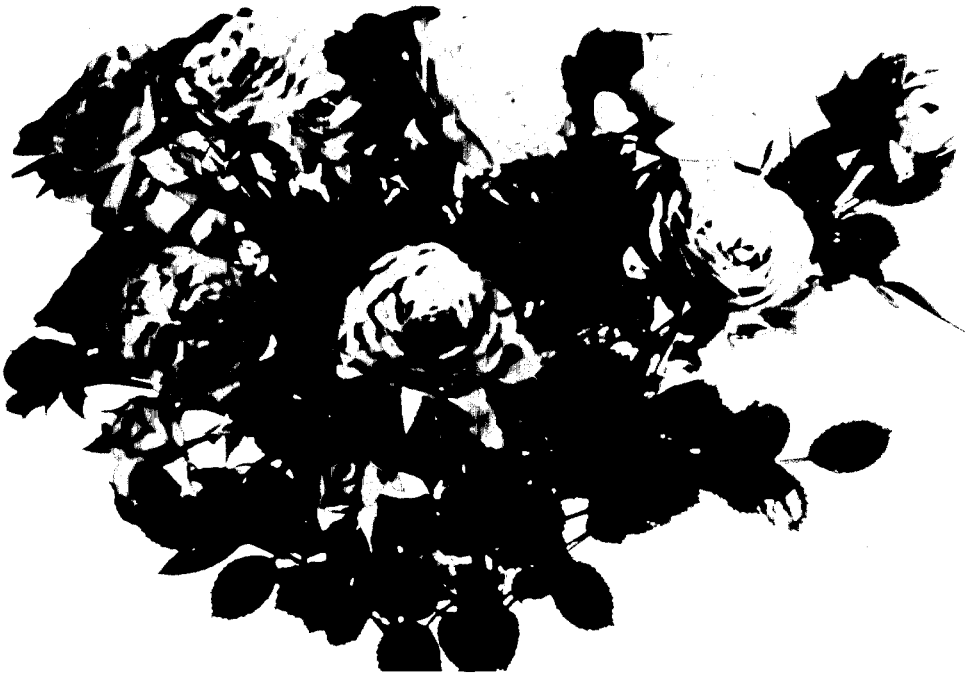

* * * * *